(12) United States Patent
Errico et al.

(10) Patent No.: US 11,419,639 B2
(45) Date of Patent: Aug. 23, 2022

(54) MODULAR OFFSET SCREW

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 371 days.

(21) Appl. No.: 16/498,722

(22) PCT Filed: Mar. 28, 2018

(86) PCT No.: PCT/US2018/024829
§ 371 (c)(1),
(2) Date: Sep. 27, 2019

(87) PCT Pub. No.: WO2018/183486
PCT Pub. Date: Oct. 4, 2018

(65) Prior Publication Data
US 2020/0038067 A1    Feb. 6, 2020

Related U.S. Application Data

(60) Provisional application No. 62/478,698, filed on Mar. 30, 2017, provisional application No. 62/478,686, filed on Mar. 30, 2017.

(51) Int. Cl.
*A61B 17/70* (2006.01)
*A61B 17/86* (2006.01)
*A61B 17/00* (2006.01)

(52) U.S. Cl.
CPC ...... *A61B 17/7041* (2013.01); *A61B 17/7076* (2013.01); *A61B 17/863* (2013.01);
(Continued)

(58) Field of Classification Search
CPC ............ A61B 17/7041; A61B 17/7005; A61B 17/7007; A61B 17/7032; A61B 17/7035;
(Continued)

(56) References Cited

U.S. PATENT DOCUMENTS 5,382,248 A    1/1995  Jacobson et al.
5,487,744 A    1/1996  Howland
(Continued)

OTHER PUBLICATIONS

International Search Report for PCT/US2018/024829 dated Aug. 3, 2018.

*Primary Examiner* — Eduardo C Robert
*Assistant Examiner* — Christina Negrellirodriguez
(74) *Attorney, Agent, or Firm* — Lerner, David, Littenberg, Krumholz & Mentlik, LLP

(57) ABSTRACT

A modular screw includes a first assembly and a second assembly. The first assembly includes a base portion having a head portion, a securing portion defining a first bore, and a receiving portion defining a second bore. The second assembly includes a first post, a second post including an engaging portion, and an elongate screw threadably engageable with the second post. The second post is dimensioned to be received through the second bore of the receiving portion of the first assembly such that when a first set screw is received in the first bore, the first set screw secures the base portion of the first assembly to the second post. The elongate screw received in the second post causes radial expansion of the engaging portion of the second post, which, in turn, causes the engaging portion to be affixed to the cavity of the first post.

20 Claims, 13 Drawing Sheets

(52) U.S. Cl.
CPC ....... *A61B 17/8605* (2013.01); *A61B 17/8635* (2013.01); *A61B 17/8685* (2013.01); *A61B 2017/00526* (2013.01)

(58) Field of Classification Search
CPC ............ A61B 17/7037; A61B 17/7076; A61B 17/8605; A61B 17/863; A61B 17/8635; A61B 17/8685; A61B 2017/00526; A61B 17/7046
USPC .................................. 606/246–279, 300–328
See application file for complete search history.

(56) References Cited

U.S. PATENT DOCUMENTS

| | | | |
|---|---|---|---|
| 5,609,592 A * | 3/1997 | Brumfield | A61B 17/7047 606/250 |
| 5,725,528 A | 3/1998 | Errico et al. | |
| 5,735,851 A | 4/1998 | Errico et al. | |
| 5,800,435 A | 9/1998 | Errico et al. | |
| 6,004,322 A | 12/1999 | Bernstein | |
| 6,050,997 A | 4/2000 | Mullane | |
| 6,146,383 A | 11/2000 | Studer et al. | |
| 6,482,207 B1 | 11/2002 | Errico | |
| 6,623,485 B2 | 9/2003 | Doubler et al. | |
| 6,669,697 B1 | 12/2003 | Pisharodi | |
| 6,887,242 B2 * | 5/2005 | Doubler | A61B 17/7035 606/274 |
| 7,163,538 B2 * | 1/2007 | Altarac | A61B 17/7035 606/86 A |
| 7,186,255 B2 | 3/2007 | Baynham et al. | |
| 7,314,467 B2 | 1/2008 | Howland | |
| 7,722,645 B2 | 5/2010 | Bryan | |
| 7,766,943 B1 | 8/2010 | Fallin et al. | |
| 8,007,518 B2 | 8/2011 | Winslow et al. | |
| 8,012,181 B2 | 9/2011 | Winslow et al. | |
| 8,016,861 B2 | 9/2011 | Mitchell et al. | |
| 8,048,115 B2 | 11/2011 | Winslow et al. | |
| 8,048,126 B2 | 11/2011 | Altarac et al. | |
| 8,057,515 B2 | 11/2011 | Flynn et al. | |
| 8,075,603 B2 | 12/2011 | Hammill, Sr. et al. | |
| 8,083,772 B2 | 12/2011 | Winslow et al. | |
| 8,083,775 B2 | 12/2011 | Winslow et al. | |
| 8,083,777 B2 | 12/2011 | Butters et al. | |
| 8,092,501 B2 | 1/2012 | Mitchell et al. | |
| 8,097,024 B2 | 1/2012 | Winslow et al. | |
| 8,114,134 B2 | 2/2012 | Winslow et al. | |
| 8,137,384 B2 | 3/2012 | Heiges et al. | |
| 8,192,468 B2 | 6/2012 | Biedermann et al. | |
| 8,192,470 B2 | 6/2012 | Biedermann et al. | |
| 8,197,518 B2 | 6/2012 | Hammill, Sr. et al. | |
| 8,211,155 B2 | 7/2012 | Winslow et al. | |
| 8,257,397 B2 | 9/2012 | Winslow et al. | |
| 8,333,792 B2 | 12/2012 | Winslow et al. | |
| 8,337,530 B2 | 12/2012 | Hestad et al. | |
| 8,337,536 B2 | 12/2012 | Mitchell et al. | |
| 8,430,916 B1 | 4/2013 | Winslow et al. | |
| 8,506,609 B2 | 8/2013 | Biedermann et al. | |
| 8,518,085 B2 | 8/2013 | Winslow et al. | |
| 8,636,781 B2 | 1/2014 | Biedermann et al. | |
| 8,636,782 B2 | 1/2014 | Biedermann et al. | |
| 8,663,290 B2 | 3/2014 | Doubler et al. | |
| 8,663,291 B2 | 3/2014 | Doubler et al. | |
| 8,881,358 B2 | 11/2014 | Biedermann et al. | |
| 8,900,270 B2 | 12/2014 | Fauth et al. | |
| 8,926,671 B2 | 1/2015 | Biedermann et al. | |
| 8,961,568 B2 | 2/2015 | McKinley et al. | |
| 8,979,904 B2 | 3/2015 | Jackson et al. | |
| 8,986,349 B1 | 3/2015 | German et al. | |
| 8,992,579 B1 | 3/2015 | Gustine et al. | |
| 8,998,958 B2 | 4/2015 | Dauster et al. | |
| 9,017,390 B2 | 4/2015 | Biedermann et al. | |
| 9,044,273 B2 | 6/2015 | Richelsoph et al. | |
| 9,060,814 B2 | 6/2015 | Doubler et al. | |
| 9,066,759 B2 | 6/2015 | Biedermann et al. | |
| 9,119,674 B2 | 9/2015 | Matthis et al. | |
| 9,131,971 B2 | 9/2015 | Biedermann et al. | |
| 9,173,684 B2 | 11/2015 | Biedermann et al. | |
| 9,186,187 B2 | 11/2015 | Mishra | |
| 9,198,694 B2 | 12/2015 | Mishra et al. | |
| 9,247,965 B2 | 2/2016 | Biedermann et al. | |
| 9,254,150 B2 | 2/2016 | Biedermann et al. | |
| 9,277,938 B2 | 3/2016 | Biedermann et al. | |
| 9,277,941 B2 | 3/2016 | Biedermann et al. | |
| 9,277,942 B2 | 3/2016 | Biedermann et al. | |
| 9,333,016 B2 | 5/2016 | Biedermann et al. | |
| 9,339,304 B2 | 5/2016 | Biedermann et al. | |
| 9,358,047 B2 | 6/2016 | Mishra et al. | |
| 9,364,266 B2 | 6/2016 | Biedermann et al. | |
| 9,439,680 B2 | 9/2016 | Biedermann et al. | |
| 9,451,990 B2 | 9/2016 | Fauth et al. | |
| 9,452,006 B2 | 9/2016 | Biedermann et al. | |
| 9,486,246 B2 | 11/2016 | Biedermann et al. | |
| 9,492,204 B2 | 11/2016 | Biedermann et al. | |
| 9,517,089 B1 * | 12/2016 | Casey | A61B 17/7041 |
| 9,579,125 B2 | 2/2017 | Raju et al. | |
| 9,603,635 B2 | 3/2017 | Leff et al. | |
| 9,615,858 B2 | 4/2017 | Doubler et al. | |
| 9,649,142 B2 | 5/2017 | Doubler et al. | |
| 9,693,808 B2 | 7/2017 | Fauth et al. | |
| 9,707,013 B2 | 7/2017 | Rezach et al. | |
| 9,820,780 B2 | 11/2017 | Duncan et al. | |
| 9,883,892 B2 | 2/2018 | Jackson et al. | |
| 9,895,170 B2 | 2/2018 | Biedermann et al. | |
| 9,895,171 B2 | 2/2018 | Webb | |
| 9,907,574 B2 | 3/2018 | Jackson et al. | |
| 9,918,745 B2 | 3/2018 | Jackson et al. | |
| 9,936,983 B2 | 4/2018 | Mesiwala et al. | |
| 9,980,753 B2 | 5/2018 | Jackson et al. | |
| 2003/0060823 A1 | 3/2003 | Bryan | |
| 2010/0057135 A1 | 3/2010 | Heiges et al. | |
| 2011/0118783 A1 | 5/2011 | Winslow et al. | |
| 2011/0245876 A1 * | 10/2011 | Brumfield | A61B 17/7035 606/264 |
| 2011/0307018 A1 | 12/2011 | Zucherman et al. | |
| 2012/0041490 A1 | 2/2012 | Jacob et al. | |
| 2014/0243900 A1 | 8/2014 | Ark et al. | |
| 2015/0196338 A1 | 7/2015 | Biedermann et al. | |
| 2016/0030086 A1 | 2/2016 | Mishra | |
| 2016/0030090 A1 | 2/2016 | Webb | |
| 2016/0220277 A1 | 8/2016 | Rezach et al. | |
| 2016/0302833 A9 | 10/2016 | Baynham | |
| 2017/0020574 A1 | 1/2017 | Biedermann et al. | |
| 2017/0049482 A1 | 2/2017 | Campbell et al. | |
| 2017/0049484 A1 | 2/2017 | Leff et al. | |
| 2017/0065306 A1 | 3/2017 | Fauth et al. | |
| 2017/0112542 A1 | 4/2017 | Biedermann et al. | |
| 2017/0172630 A1 | 6/2017 | Biedermann et al. | |
| 2017/0224386 A1 | 8/2017 | Leff et al. | |
| 2017/0245898 A1 | 8/2017 | May et al. | |
| 2017/0333085 A1 | 11/2017 | Jackson et al. | |
| 2018/0014858 A1 | 1/2018 | Biester et al. | |
| 2018/0014862 A1 | 1/2018 | Raina et al. | |
| 2018/0014863 A1 | 1/2018 | Biester et al. | |
| 2018/0036039 A1 | 2/2018 | Biedermann et al. | |
| 2018/0055545 A1 | 3/2018 | Biedermann et al. | |
| 2018/0092679 A1 | 4/2018 | Toon et al. | |
| 2018/0110548 A1 | 4/2018 | May et al. | |

* cited by examiner

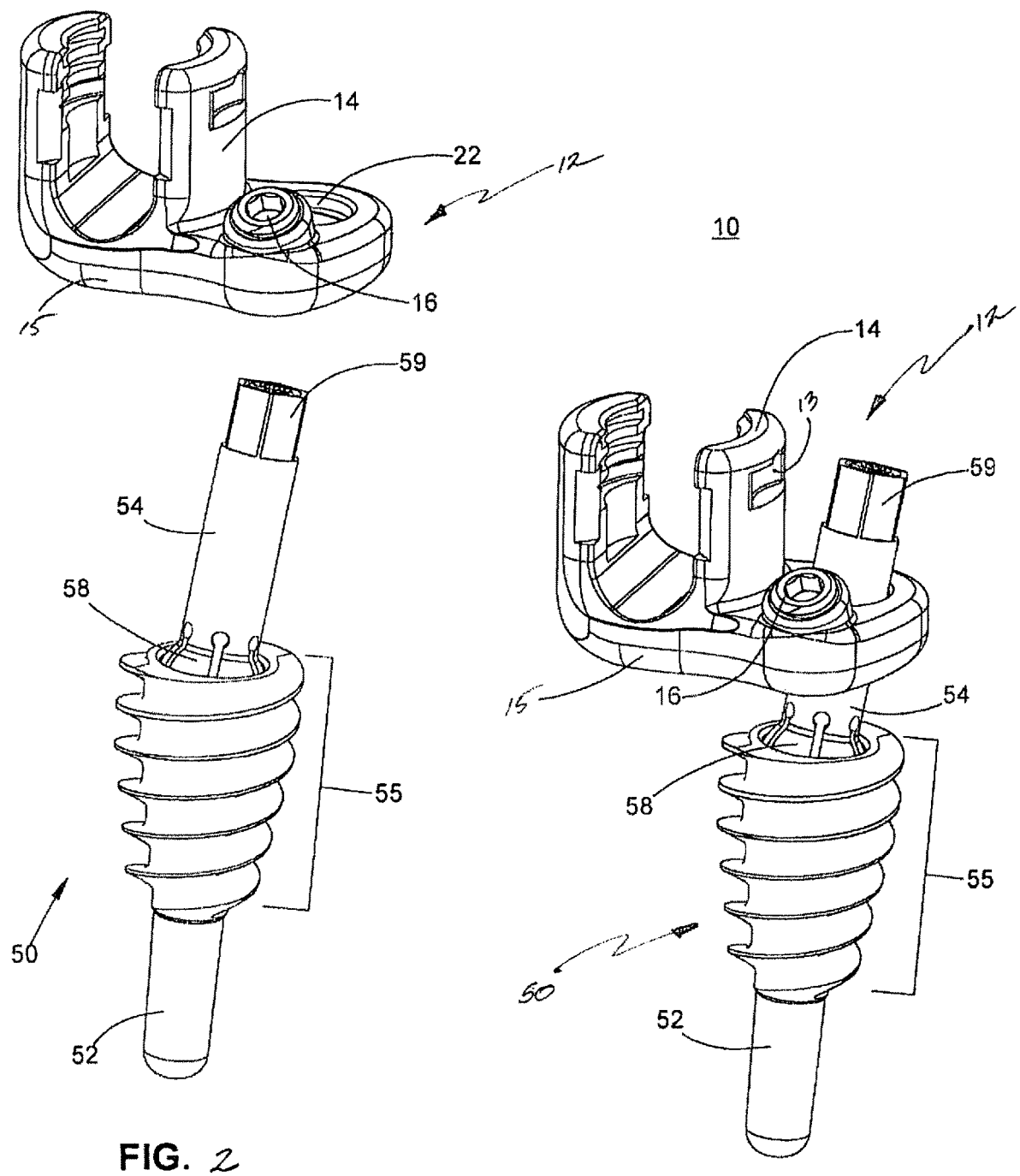

MODULAR OFFSET SCREW

CROSS-REFERENCE TO RELATED APPLICATIONS

This application is a national phase entry under 35 U.S.C. § 371 of International Application No. PCT/US2018/024829, filed Mar. 28, 2018, which claims priority to, and the benefit of, U.S. Provisional Patent Application Ser. Nos. 62/478,686, filed on Mar. 30, 2017, and 62/478,698, filed on Mar. 30, 2017, the entire contents of each of which are incorporated by reference herein.

BACKGROUND

Technical Field

The present disclosure relates to a device for spinal surgery and, more particularly, to a modular offset screw.

Background of Related Art

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal spinal rods or plates. When the spine surgery is performed posteriorly, it is common practice to place bone screws into the vertebral bodies and then connect a metal rod between the screws, thus creating a rigid structure between adjacent vertebral bodies. In some cases, the use of these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body. Because different patients have different anatomies, there exists the potential that the screws may be inserted at different angles and at different heights relative to the operating field.

Therefore, a continuing need exists for an improved fixation member that could reduce the time and labor required by a user to insert the fixation member, such as a screw, into a vertebra, while also providing the ability to adjust the angle and the height to ensure proper placement of medical hardware, such as spinal rods and bands.

SUMMARY

The present disclosure describes a modular screw that demonstrates a practical approach to meeting the performance requirements and overcoming usability challenges associated with spinal surgeries. In accordance with an embodiment of the present disclosure, a modular screw includes a first assembly and a second assembly. The first assembly includes a base portion having a head portion defining a slot dimensioned to receive a spinal rod, a securing portion defining a first bore and including a first set screw threadably received in the first bore, and a receiving portion defining a second bore. The second assembly is operatively associated with the first assembly. The second assembly includes a first post defining a cavity, a second post including an engaging portion rotatably received in the cavity of the first post, and an elongate screw threadably engageable with the second post. In particular, the second post is dimensioned to be received through the second bore of the receiving portion of the first assembly such that when the first set screw of the securing portion is received in the first bore of the securing portion, the first set screw secures the base portion of the first assembly to the second post. The elongate screw received in the second post causes radial expansion of the engaging portion of the second post, which, in turn, causes the engaging portion to be affixed to the cavity of the first post.

In an embodiment, the engaging portion of the second post and the cavity of the first post may have a ball and socket configuration.

In another embodiment, the engaging portion of the second post may define a slit configured to enable radial expansion of the engaging portion.

In yet another embodiment, the receiving portion of the first assembly may define an annular groove concentrically arranged with the second bore.

In still yet another embodiment, the second post may define internal threads configured to threadably engage the elongate screw.

In an embodiment, the receiving portion of the first assembly may include a ring defining a slit configured to provide radial contraction and expansion of the ring. In particular, the ring may be configured to contract when the first set screw is threadably received in the first bore of the securing portion.

In another embodiment, a first longitudinal axis defined by the first bore of the first assembly may define an acute angle with respect to a second longitudinal axis defined by the second bore.

In yet another embodiment, the first post of the second assembly may include external threads along a length of the first post.

In still yet another embodiment, at least a portion of the first post may be tapered along a length thereof.

In still yet another embodiment, the at least a portion of the first post may extend at least a quarter of the length of the first post.

In still yet another embodiment, the first post of the second assembly may include an inner surface having a keyed surface distal of the cavity.

In still yet another embodiment, the head portion of the first assembly may define a lateral opening configured to receive a band therethrough.

In an embodiment, the head portion of the first assembly may include inner walls defining internal threads configured to threadably engage a set screw configured to secure the spinal rod received in the slot.

In another embodiment, the second post may be configured for a polyaxial range of motion with respect to the first post. The polyaxial motion may define an angle with respect to a longitudinal axis defined by the first post in the range of about 15 degrees and about 60 degrees.

In accordance with another embodiment of the present disclosure, a modular screw includes a first assembly and a second assembly. The first assembly includes a base portion including a first set screw and a head portion configured to receive a spinal rod, the base portion defining a first bore configured to threadably receive the first set screw, and a second bore. The second assembly includes a first post configured to be at least partially received in tissue, a second post operatively associated with the first post, and an elongate screw operatively coupled with the second post to secure a relative orientation of the second post with respect to the first post. The second post is dimensioned to be received in the second bore of the first assembly, whereby a distance between the base portion of the first assembly and the first post is selectively adjustable.

In an embodiment, the first bore of the base portion may define a first axis and the second bore of the base portion may define a second axis. The first and second axes may define an acute angle with respect to each other.

In another embodiment, the second post of the second assembly may include an engaging portion transitionable between a radially expanded state and a radially contracted state, wherein the engaging portion is configured to maintain the orientation of the second post with respect to the first post when the engaging portion is in the radially expanded state.

In yet another embodiment, the first post may include a tapered portion extending along a length of the first post.

In still yet another embodiment, the tapered portion may extend partially along the length of the first post.

In still yet another embodiment, the tapered portion may include external threads.

In accordance with another embodiment of the present disclosure, a post for use with a modular screw assembly includes a head including a keyed inner surface having a key feature for engagement with a driver, a tapered portion having external threads tapered along a length of the tapered portion, and a shank extending distally from the tapered portion. The tapered portion extends at least a quarter of a length of the post.

In an embodiment, the tapered portion may extend at least a half of a length of the post.

In another embodiment, a major diameter of the external threads of the tapered portion may be in the range of about 9 mm and about 13 mm.

In yet another embodiment, the major diameter of the external threads may be in the range of about 10 mm and about 12 mm.

In still yet another embodiment, the major diameter may taper along the length of the post at a ratio of a major diameter at a proximal portion of the tapered portion to a major diameter at a distal portion of the tapered portion in the range of about 1 and about 2.

In an embodiment, the ratio may be in the range of about 1.4 and about 1.7.

In another embodiment, an angle of taper of the tapered portion with respect to a longitudinal axis defined by the tapered portion may be in the range of about 10 degrees and about 60 degrees.

In yet another embodiment, the angle of taper of the tapered portion may be in the range of about 18 degrees and 56 degrees.

In still yet another embodiment, a diameter of the post may be in the range of about 2 mm and 5 mm.

In still yet another embodiment, the diameter of the post may be in the range of about 3 mm and 4 mm.

In still yet another embodiment, the shank may extend at least a half of a length of the post.

In still yet another embodiment, the shank may have a smooth surface.

In still yet another embodiment, the shank may include a gripping surface.

In still yet another embodiment, the gripping surface may include shallow helical threads.

In accordance with another embodiment of the present disclosure, a post for use with a modular screw assembly includes a housing assembly and a post. The housing assembly includes a base portion having a head portion defining a slot, a securing portion defining a first bore, and a receiving portion defining a second bore. The post includes a head, a tapered portion including threads, and a shaft extending distally from the tapered portion. A proximal portion of the head includes a multi-faceted surface configured to engage a tool. The head is configured to be slidably received in the second bore of the housing assembly.

In an embodiment, the securing portion of the housing assembly may include a first set screw configured to secure the base portion to the head of the post when the head of the post is inserted through the second bore of the housing assembly.

BRIEF DESCRIPTION OF THE DRAWINGS

Various embodiments of the present disclosure are described hereinbelow with reference to the drawings, wherein:

FIG. 1 is a perspective view of a modular screw in accordance with an embodiment of the present disclosure;

FIG. 2 is a perspective view of the modular screw of FIG. 1 with a first assembly and a second assembly separated;

DETAILED DESCRIPTION

Figure 3:
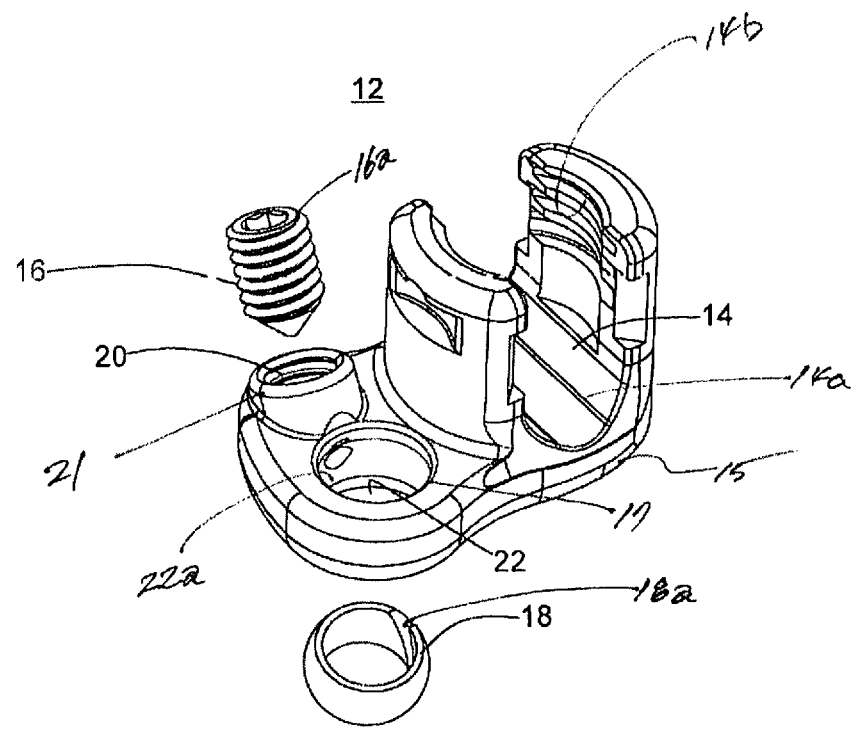
FIG. 3 is an exploded perspective view of the first assembly of FIG. 2 with parts separated.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1 and 2, an embodiment of the present disclosure is shown generally as a modular screw 10 that is configured and adapted for use in a spinal surgical procedure. The modular screw 10 includes a first assembly 12 and a second assembly 50. The first assembly 12 is selectively securable with the second assembly 50. The modular screw 10 provides the ability to selectively adjust the angle and the height to ensure proper placement of spinal rods and bands as will be described in detail hereinafter.

Figure 4:
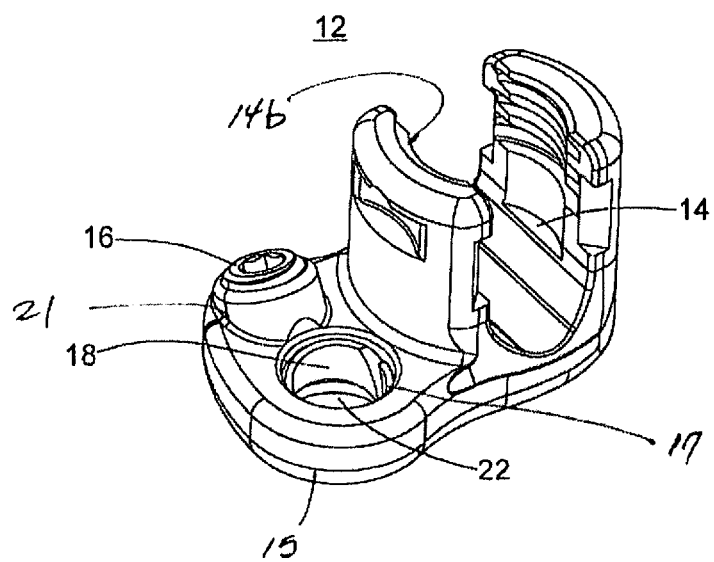
FIG. 4 is a perspective view of the first assembly of FIG. 3.

With reference now to FIGS. 3 and 4, the first assembly 12 includes a base portion 15 including a head portion 14, a receiving portion 17, and a securing portion 21. The head portion 14 extends proximally from the base portion 15, and defines a slot 14a configured to receive, e.g., a spinal rod or a band (not shown). The slot 14a may include an arcuate profile to facilitate securement of the spinal rod therein. The head portion 14 includes inner walls 14b having threads configured to threadably receive a set screw (not shown) to secure the spinal rod in the slot 14a. In one embodiment, the inner walls 14b may further define lateral openings 13 (FIG. 1) configured to receive a band. Reference may be made to U.S. Pat. Nos. 8,814,919 and 9,393,049, the entire contents of each of which are incorporated herein by reference, for a detailed description of the construction and operation of taper lock or set screw housing systems.

With continued reference to FIGS. 3 and 4, the securing portion 21 defines a first bore 20 and includes a set screw 16 dimensioned to be threadably received in the first bore 20. The receiving portion 17 defines a second bore 22 and a split ring 18 defining a slit 18a configured to enable radial contraction and expansion of the split ring 18 to selectively engage a polyaxial post 54 (FIG. 2) of the second assembly 50. In particular the first bore 20 may define, e.g., an acute angle, with respect to the second bore 22 such that when the set screw 16 is threadably received in the first bore 20, the set screw 16 engages at least a portion of the split ring 18 disposed in the second bore 22, which, in turn, causes radial contraction of the split ring 18 to frictionally engage the polyaxial post 54 (FIG. 2) of the second assembly 50. In this manner, the first assembly 12 may be selectively secured at a position along a length of the polyaxial post 54 of the second assembly 50. The set screw 16 includes a proximal portion 16a defining a cavity 16a having, e.g., a hex, key feature for non-slip engagement with a driver or other instrument (not shown) to drive the set screw 16. It is contemplated that the cavity 16a may have any suitable configuration such as, e.g., slotted, square, star, or a Phillips head, for engagement with the driver.

With continued reference to FIGS. 3 and 4, the receiving portion 17 defines the second bore 22 and an annular groove 22a concentrically arranged with the second bore 22. The receiving portion 17 includes the split ring 18 mounted in the annular groove 22a such that the split ring 18 is transitionable between a radially expanded state and a radially contracted state. The annular groove 22a inhibits axial displacement of the split ring 18 relative to the base portion 15. The second bore 22 and the split ring 18 are dimensioned to receive the polyaxial post 54 of the second assembly 50 therethrough. Under such a configuration, when the set screw 16 is threadably received in the first bore 20, the set screw 16 engages the split ring 18 and transitions the split ring 18 to the contracted state, which, in turn, frictionally secures the base portion 15 on a position along a length of the polyaxial post 54.

Figure 5A:
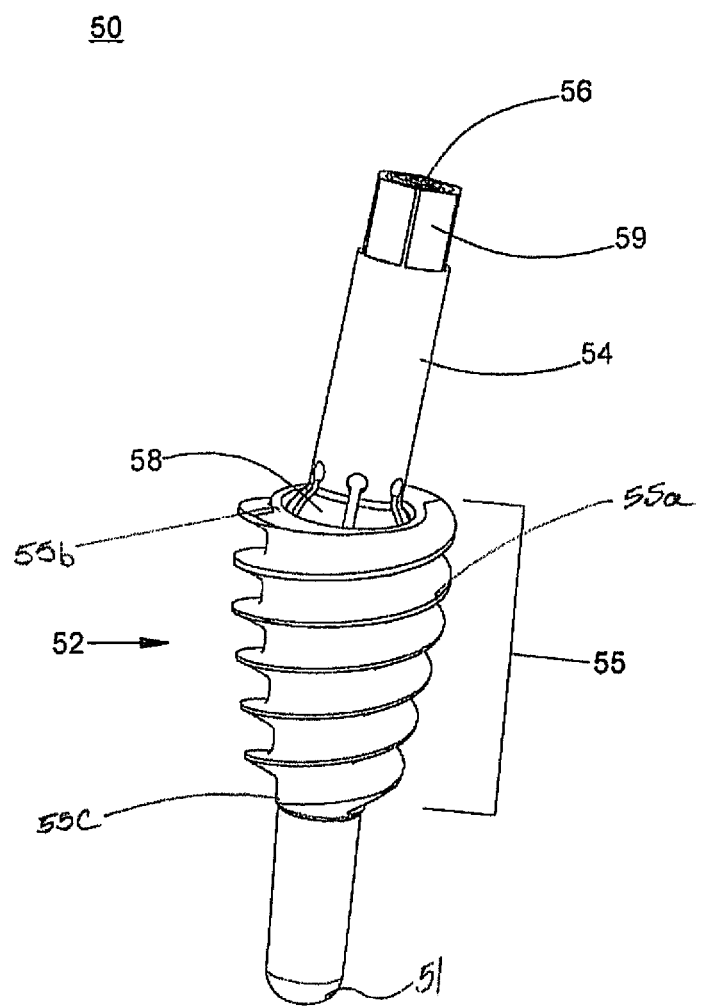
FIG. 5A is a perspective view of the second assembly of FIG. 2.
Figure 5B:
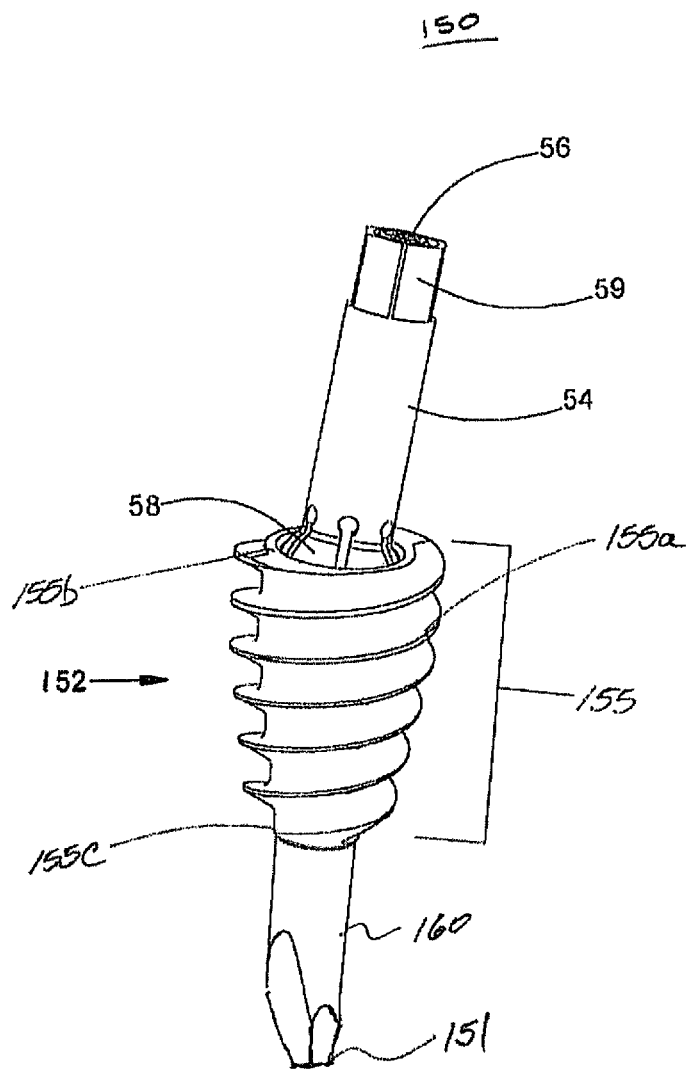
FIG. 5B is a perspective view of a second assembly in accordance with another embodiment of the present disclosure.
Figure 6:
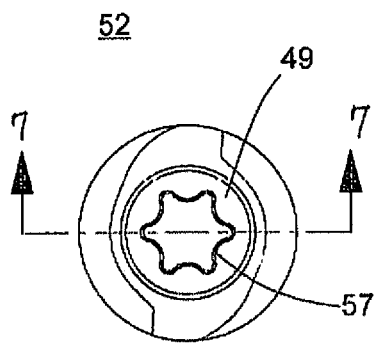
FIG. 6 is a top view of a post of the second assembly of FIG. 5.
Figure 7:
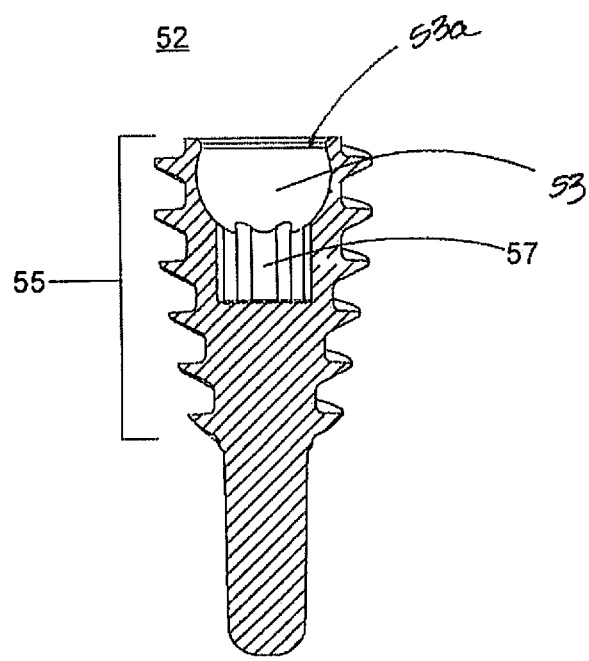
FIG. 7 is a side cross-sectional view of the post of FIG. 6 cut along section line 7-7 of FIG. 6.

With reference now to FIGS. 5-7, the second assembly 50 includes a post 52, a polyaxial post 54, and an elongate screw 56. The post 52 defines a cavity 53 having an opening 53a dimensioned to receive a distal portion 58 of the polyaxial post 54. In particular, the cavity 53 may have a shape that is complementary to a distal portion 58 of the polyaxial post 54. For example, the cavity 53 may include an arcuate or concave profile to receive a bulbous shape of the distal portion 58 of the polyaxial post 54 for polyaxial movement of the polyaxial post 54 relative to the post 52. The post 52 includes a tapered portion 55 extending along a length of the post 52. For example, the tapered portion 55 may extend at least a quarter of the length of the post 52. In addition, the tapered portion 55 may extend at least a half of the length of the post 52. Alternatively, the tapered portion 55 may be less than a quarter of the length of the implant. The tapered portion 55 includes external threads 55a configured to engage, e.g., osseous tissue. The tapered portion 55 may include a major diameter in the range of about 9 mm and about 13 mm. Furthermore, the tapered portion 55 may include a major diameter in the range of about 10 mm and about 12 mm. The major diameter may be tapered along the length of the post 52 at a ratio of major diameter at the proximal portion 55b of the tapered portion 55 to a major diameter at the distal portion 55c of the tapered portion 55 in the range of about 1 and about 2. Alternatively, the ratio may be in the range of about 1.4 and about 1.7. For example, an angle of the taper may vary from about 10 degrees to about 60 degrees. Furthermore, the angle may vary from about 18 degrees to about 56 degrees. The post 52 may include a diameter in the range of about 2 mm and 5 mm. Furthermore, the diameter of the post 52 may be in the range of about 3 mm and about 4 mm.

With reference to FIG. 5B, a second assembly 150 in accordance with another embodiment of the present disclosure includes a post 152, a poly axial post 54, and an elongate screw 56. The post 152 is substantially identical to the post 52. In particular, the post 152 defines a cavity (not shown) having an opening (not shown) dimensioned to receive a distal portion 58 of the polyaxial post 54 for polyaxial movement of the polyaxial post 54 relative to the post 152. The post 152 includes a tapered portion 155 extending along a length of the post 152. For example, the tapered portion 155 may extend at least a quarter of the length of the post 152. In addition, the tapered portion 155 may extend at least a half of the length of the post 152. Alternatively, the tapered portion 155 may be less than a quarter of the length of the implant. The tapered portion 155 includes external threads 155a configured to engage, e.g., osseous tissue. The post 152 further includes a distal portion 160 distal of the tapered portion 155. The distal portion 160 includes a non-threaded surface. While the post 52 (FIG. 5A) is shown to have an atraumatic blunt tip 51, it is contemplated that the post 152 may include a pointed tip 151.

Figure 8:
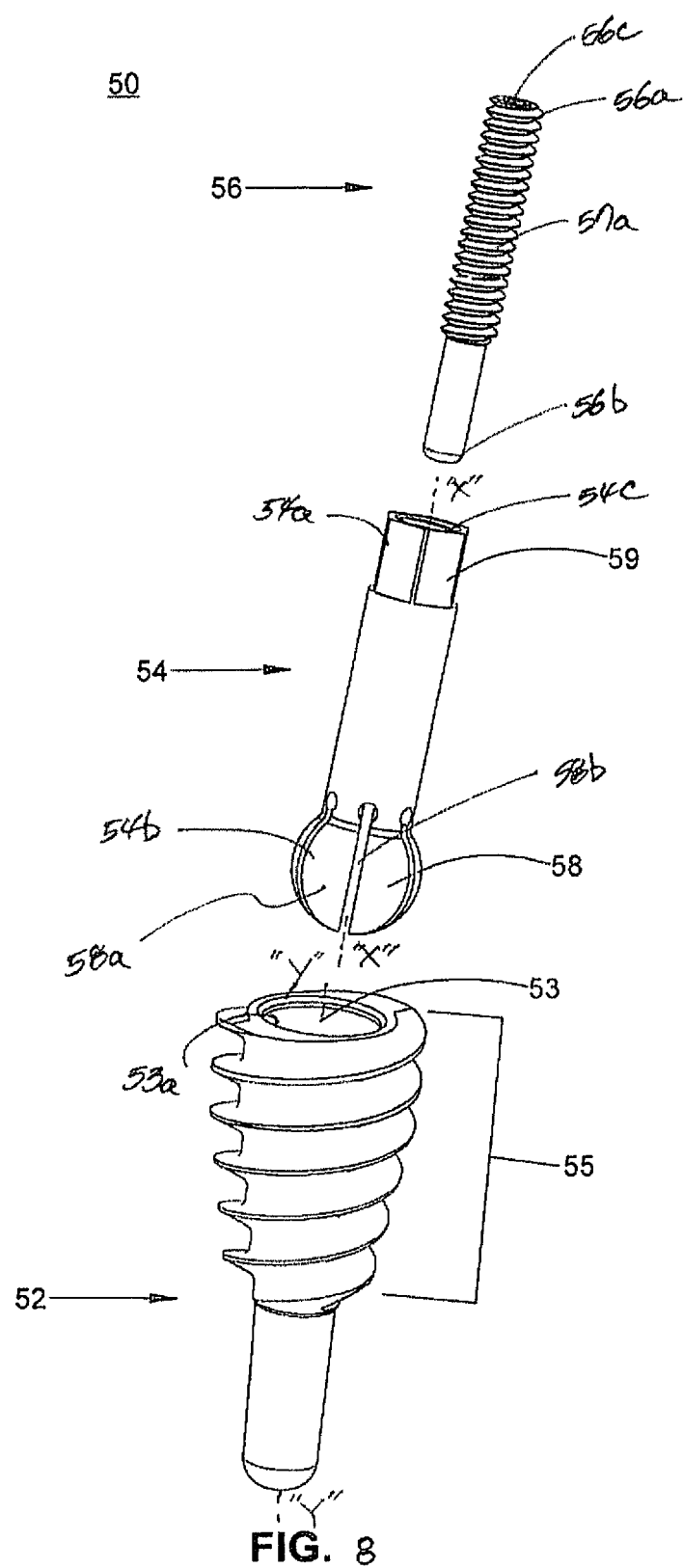
FIG. 8 is an exploded perspective view of the second assembly of FIG. 5 with parts separated.
Figure 10:
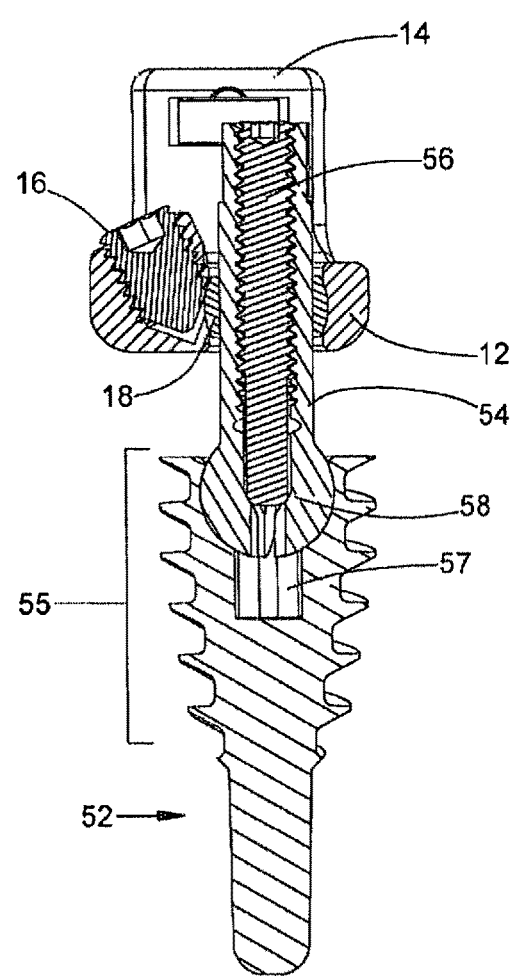
FIG. 10 is a side cross-sectional view of the modular screw of FIG. 9 cut along section line 10-10 of FIG. 9.
Figure 11:
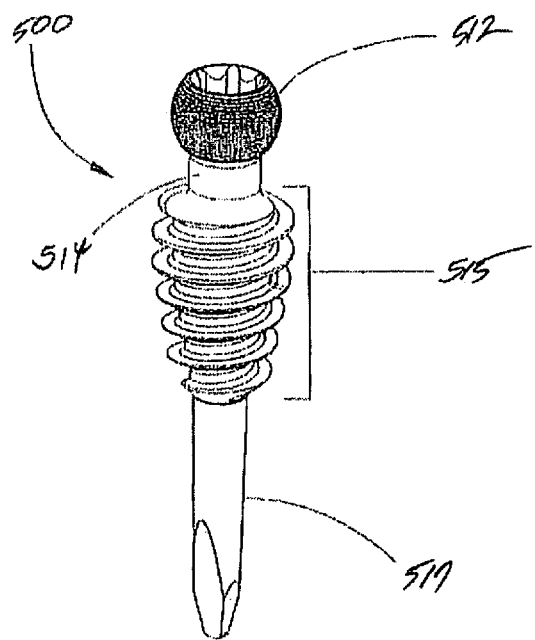
FIG. 11 is a perspective view of a post for use with a modular screw assembly in accordance with an embodiment of the present disclosure.
Figure 12:
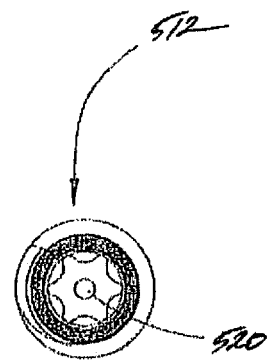
FIG. 12 is a top view of the post of FIG. 11.

With brief reference to FIG. 10, the post 52 may further include a keyed inner surface 57 distal of the cavity 53 (FIG. 8). The keyed inner surface 57 may include, e.g., a hex, key feature for non-slip engagement with a driver or other instrument (not shown) to drive the post 52. It is contemplated that the keyed inner surface 57 may have any suitable configuration such as, e.g., slotted, square, star, or a Phillips head, for engagement with the driver.

With reference now to FIG. 8, the polyaxial post 54 of the second assembly 50 includes a proximal portion 54a and a distal portion 54b. The proximal portion 54a may include a multi-faceted outer surface 59 configured to engage a tool (not shown). The distal portion 54b includes an engaging portion 58a having a bulbous shape. The engaging portion 58a and the cavity 53 of the post 52 provide, e.g., a ball and socket configuration, to enable polyaxial movement (i.e., rotation and pivoting) of the polyaxial post 54 relative to the post 52. The engaging portion 58a defines a plurality of slits 58a extending along a length thereof. The slits 58 may be circumferentially arranged about a central longitudinal axis "X-X" of the polyaxial post 54. The plurality of slits 58a is configured to enable radial expansion of the engaging portion 58a in the presence of applied force, thereby providing, e.g., a friction fit, within the cavity 53 of the post 52. While the engaging portion 58a and cavity 53 of the post 52 may have, e.g., a ball and socket configuration, it is contemplated that other configuration may be utilized for expansion of the engaging portion 58a to enable friction fit with the cavity 53.

Figure 9:
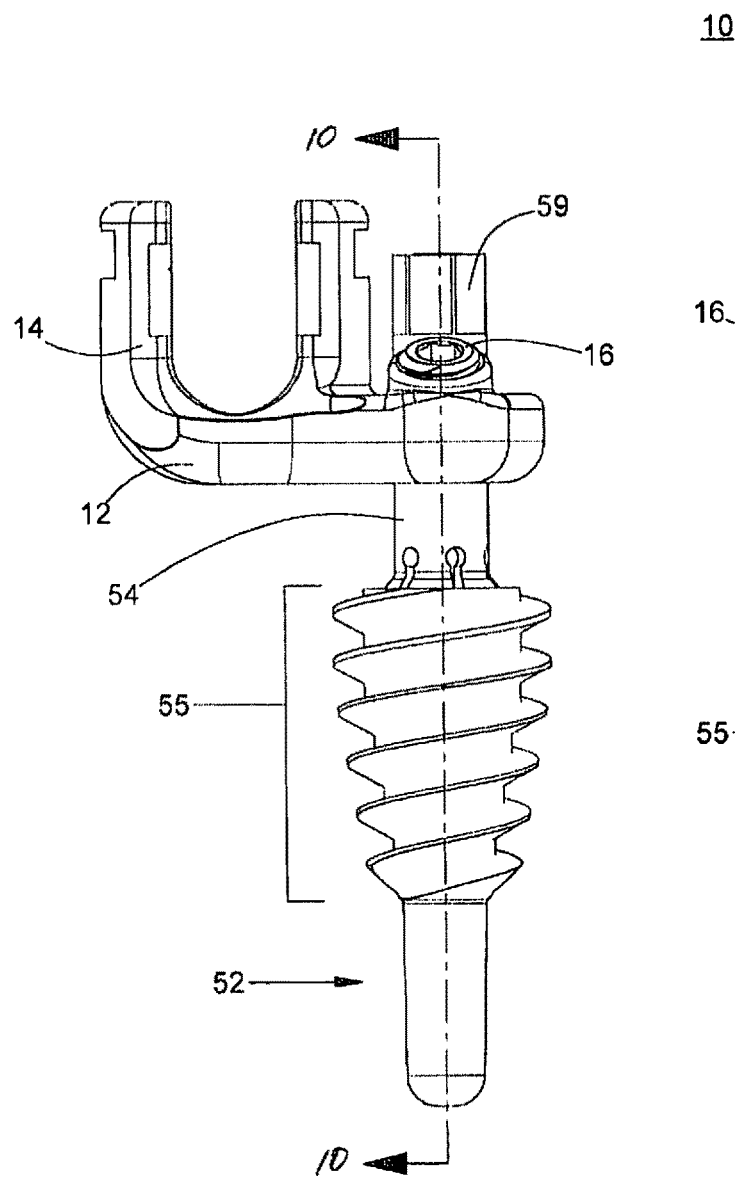
FIG. 9 is a side view of the modular screw of FIG. 1.

With continued reference to FIGS. 8-10, the polyaxial post 54 defines a channel 54c dimensioned to, e.g., threadably, receive the elongate screw 56. The elongate screw 56 includes a proximal end 56a and a distal end 56b. The proximal end 56a defines a cavity 56c having, e.g., a hex, key feature for non-slip engagement with a driver or other instrument (not shown) to drive the elongate screw 56. It is contemplated that cavity 56c may have any suitable configuration such as, e.g., slotted, square, star, or a Phillips head, for engagement with the driver. The elongate screw 56 further includes a threaded portion 57a configured to threadably engage internal threads (not shown) of the polyaxial post 54. Under such a configuration, as the elongate screw 56 is moved distally relative to the polyaxial post 54, the distal end 56b of the elongate screw 56 engages an interior of the engaging portion 58a of the polyaxial post 54 and urges the engaging portion 58a to expand radially outward. In this manner, the radially expanded engaging portion 58a engages the cavity 53 of the post 52 and enables the clinician to selectively secure the polyaxial post 54 relative to the post 52 at a desired orientation.

In this manner, the polyaxial post 54 and the elongate screw 56 may be positioned at various angles relative to a longitudinal axis "Y-Y" defined by the post 52, thereby enabling polyaxial range of motion. The angle may be in the range of about 0 degree and about 85 degrees. Alternatively, the angle may be in the range of about 5 degrees and about 75 degrees. Furthermore, the angle may be in the range of about 15 degrees and about 60 degrees. Under such a configuration, the clinician may selectively adjust the angle of the polyaxial post 54 relative to the longitudinal axis "Y-Y" of the post 52, which, in turn, adjusts a position of the first assembly 12. After a suitable angle has been selected, the clinician may threadably insert the elongate screw 56 into the channel 54c of the polyaxial post 54 in order to expand the engaging portion 58a of the polyaxial post 54 radially outward within the cavity 53 of the post 52 and thereby fixing or setting the angle through, e.g., a friction fit, between the engaging portion 58a and the cavity 53 of the post 52.

Specifically, the polyaxial post 54 and the elongate screw 56 may be fixed at a particular angle relative to the longitudinal axis "Y-Y" of the post 52 by first selecting a desired orientation of the polyaxial post 54 and threadably inserting the elongate screw 56 into the polyaxial post 54. At this time, the polyaxial post 54 may be received through the second bore 22 of the first assembly 12. In particular, the first assembly 12 is selectively positionable at any position along a length of the polyaxial post 54. In this manner, a relative distance between the first assembly 12 and the post 52 may be selectively adjustable. Upon positioning the first assembly 12 at a desired location along the length of the polyaxial post 54, the clinician may tighten the set screw 16 such that the set screw 16 engages the split ring 18, which, in turn, securely engages the polyaxial post 54.

As the slot 14a of the head portion 14 may be moved closer to or farther away from post 52 and may also be pivoted and/or rotated relative to longitudinal axis "Y-Y" of post 52, the modular screw 10 provides increased flexibility in assembling a rod and screw spinal construct. In particular, after the desired number of posts 52 is affixed to the vertebrae to define the number of levels of the construct, each first assembly 12 may be raised or lowered to a desired height for the construct. Additionally, each first assembly 12 may be rotated and/or pivoted into a desired orientation such that the slots 14a of the head portions 14 are the correct orientation for receiving a spinal rod. The ability of the head portions 14 to have rotational adjustment, pivotal adjustment, and height adjustment allows for greater flexibility in assembling a spinal rod and screw construct tailored to the procedure and the patient's anatomy In use, with reference to FIGS. 9 and 10, the clinician initially prepares the vertebrae (not shown). The clinician may form an insertion hole in, e.g., osseous tissue, by preparing the surface with a burr or other like instrument and then an awl to start the hole. The insertion hole may be formed into, e.g., a cortical shell of an upper portion of a pedicle. The tapered portion 55 of the post 52 may be inserted above and/or in, but not through, an isthmus of the pedicle such that the likelihood of breaching the pedicle and the need for navigation is eliminated. Thereafter the post 52 of the second assembly 50 may be inserted into the insertion hole. A driver (not shown) may be utilized to engage the keyed inner surface 57 of the post 52 to drive the tapered portion 55 of the post 52 into osseous tissue.

The polyaxial post 54 is inserted into the cavity 53 of the post 52. The polyaxial post 54 is selectively adjusted to a desired orientation and/or angle relative to the post 52. At this time, the elongate screw 56 is threadably inserted into the channel 54c of the polyaxial post 54 to lock or securely fix the angle of the polyaxial post 54 relative to the post 52. Thereafter, the polyaxial post 54 is inserted through the second bore 22 of the first assembly 12. A relative distance between the first assembly 12 and the post 52 of the second assembly 50 is selectively adjusted. In particular, the base portion 15 is selectively displaced at a position along a length of the polyaxial post 54. Other spinal devices may be coupled to the modular screw 10. For example, a spinal rod (not shown) may be received in the slot 14a of the head portion 14 of the first assembly 12. It is also contemplated that a band (not shown) may be received through lateral openings 13 (FIG. 1) of the head portion 14. In this manner, the modular screw 10 enables selective height and angle adjustments to enable proper fit with other spinal devices.

With reference to FIGS. 11-14, a post for use with a modular screw assembly in accordance with an embodiment of the present disclosure is shown generally as a post 500. The post 500 is configured to protect spinal nerves and eliminate the need for redirection in a spinal surgical procedure. The post 500 includes a head 512, a tapered portion 515, a neck 514 interconnecting the head 512 and the tapered portion 515, and a shank 517 extending distally from the tapered portion 515. The head 512 includes a keyed inner surface 520 having, e.g., a hex, key feature for non-slip engagement with a driver or other instrument (not shown) to drive the post 500. It is contemplated that the keyed inner surface 520 may have any suitable configuration such as, e.g., slotted, square, star, or a Phillips head, for engagement with the driver. The head 512 is configured to receive a modular screw assembly (not shown). The head 512 is configured to provide polyaxial movement with the modular screw assembly. However, the head 512 may have any shape. In addition, the head 512 may include a roughened outer surface. Reference may be made to U.S. Pat. Nos. 5,735,851; 5,725,528; and 5,800,435, the entire contents of each of which are incorporated herein by reference, for a detailed description of the construction and operation of modular screw assemblies.

Figure 13:
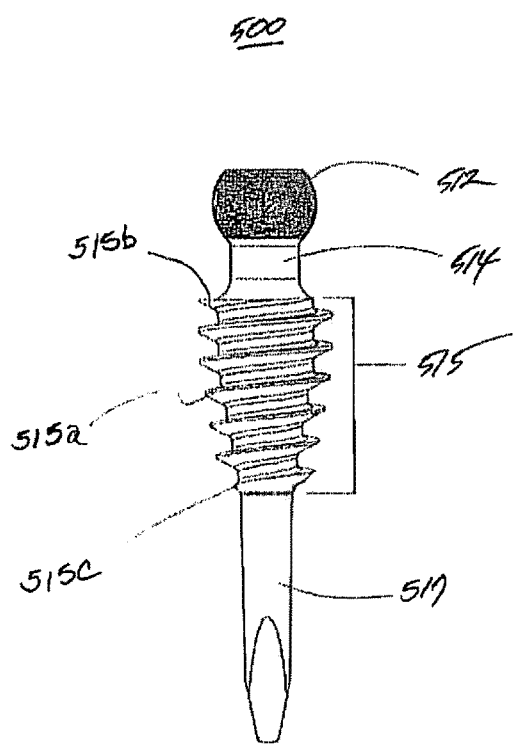
FIG. 13 is a front view of the post of FIG. 11.
Figure 14:
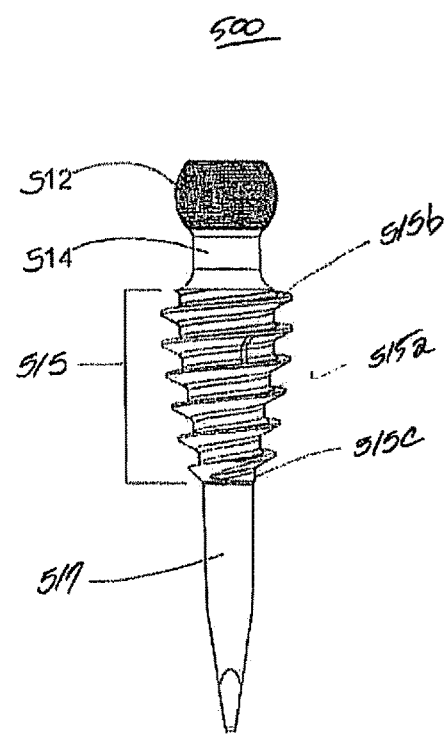
FIG. 14 is a side view of the post of FIG. 11.

With particular reference to FIGS. 13 and 14, the tapered portion 515 of the post 500 may be configured and dimensioned to fit within an isthmus of a pedicle of a vertebra. It is envisioned that the tapered portion 515 is configured to fit within or stay above the isthmus of a pedicle and inhibit the post 500 from breaching the osseous tissue. The tapered portion 515 includes helical threads 515a. For example, the tapered portion 515 may extend at least a quarter of a length of the post 500. Alternatively, the tapered portion 515 may extend at least a half of a length of the post 500. Furthermore, the tapered portion 515 may be less than a quarter of the length of the post 500. In addition, a major diameter of the helical threads 515a may be in the range of about 9 mm and about 13 mm. Alternatively, the major diameter of the helical threads 515a may be in the range of about 10 mm and about 12 mm. The major diameter tapers along the length of the post 500 at a ratio of a major diameter at a proximal portion 515b of the tapered portion 515 to a major diameter at a distal portion 515c of the tapered portion 515 in the range of about 1 and about 2. Alternatively, the ratio may be in the range of about 1.4 and about 1.7. The angle of the taper may vary from about 10 degrees to about 60 degrees. Alternatively, the angle of the taper may be in the range of about 18 degrees and 56 degrees. A diameter of the post 500 may be in the range of about 2 mm and 5 mm. In an embodiment, the diameter of the post 500 may be in the range of about 3 mm and 4 mm. The helical threads 515a may rotate clockwise or counter-clockwise about the tapered portion 515. The helical threads 515a is configured to cut into or engage with osseous tissue. The tapered portion 515 may be configured and dimensioned to be a steep taper or a narrow taper from the proximal portion 515b to the distal portion 515c.

With continued reference to FIGS. 13 and 14, the shank 517 is configured to protrude into a vertebral body. For example, the shank 517 is configured to extend through the isthmus and into the vertebral body while the tapered portion 515 resides or fits within the isthmus of a pedicle. In particular, the shank 517 may extend at least a quarter of a length of the post 500. Alternatively, the shank 517 may extend at least a half of a length of the post 500. The shank 517 may include a smooth surface. Alternatively, the shank 517 may include a gripping surface such as a shallow helical thread, a plurality of raised ridges, or any roughened surface.

In use, initially, an insertion hole is formed in osseous tissue by preparing the surface with a burr or other like instrument and then an awl to start the hole. After forming the insertion hole, the post 500 is inserted into the insertion hole. In particular, the post 500 is inserted into the insertion hole until the tapered portion 515 abuts the osseous tissue, such as, e.g., fitting with an isthmus of the osseous tissue. In this manner, the likelihood of breaching the pedicle is reduced and the need for navigation is eliminated. At this time the clinician may utilize a driver (not shown) to drive the head 512 of the post 500. In this manner, the post 500 is rotated about its longitudinal axis within the insertion hole such that the helical threads 515a of the tapered portion 515 engage the osseous tissue thereby fixing the post 500 to the osseous tissue.

Figure 15:
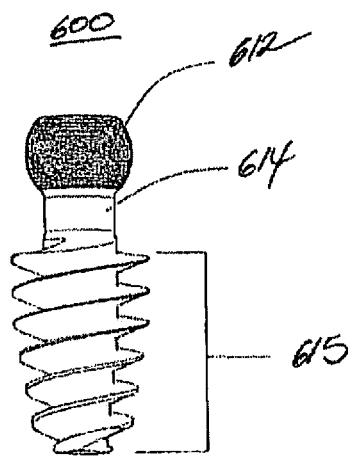
FIG. 15 is a side view of a post for use with a modular screw assembly in accordance with another embodiment of the present disclosure.

With reference now to FIG. 15, there is illustrated a post 600 in accordance with another embodiment of the present disclosure. The post 600 is substantially identical to the post 500. In particular, the post 600 includes a head 612, a tapered portion 615, and a neck 614 interconnecting the head 612 and the tapered portion 615. However, the post 600 does not include a shank extending distally from the tapered portion 615. The method of use and operation of the post 600 is substantially identical to the method of use and operation of the post 500, and thus, will not be described herein.

Figures 16, 17:
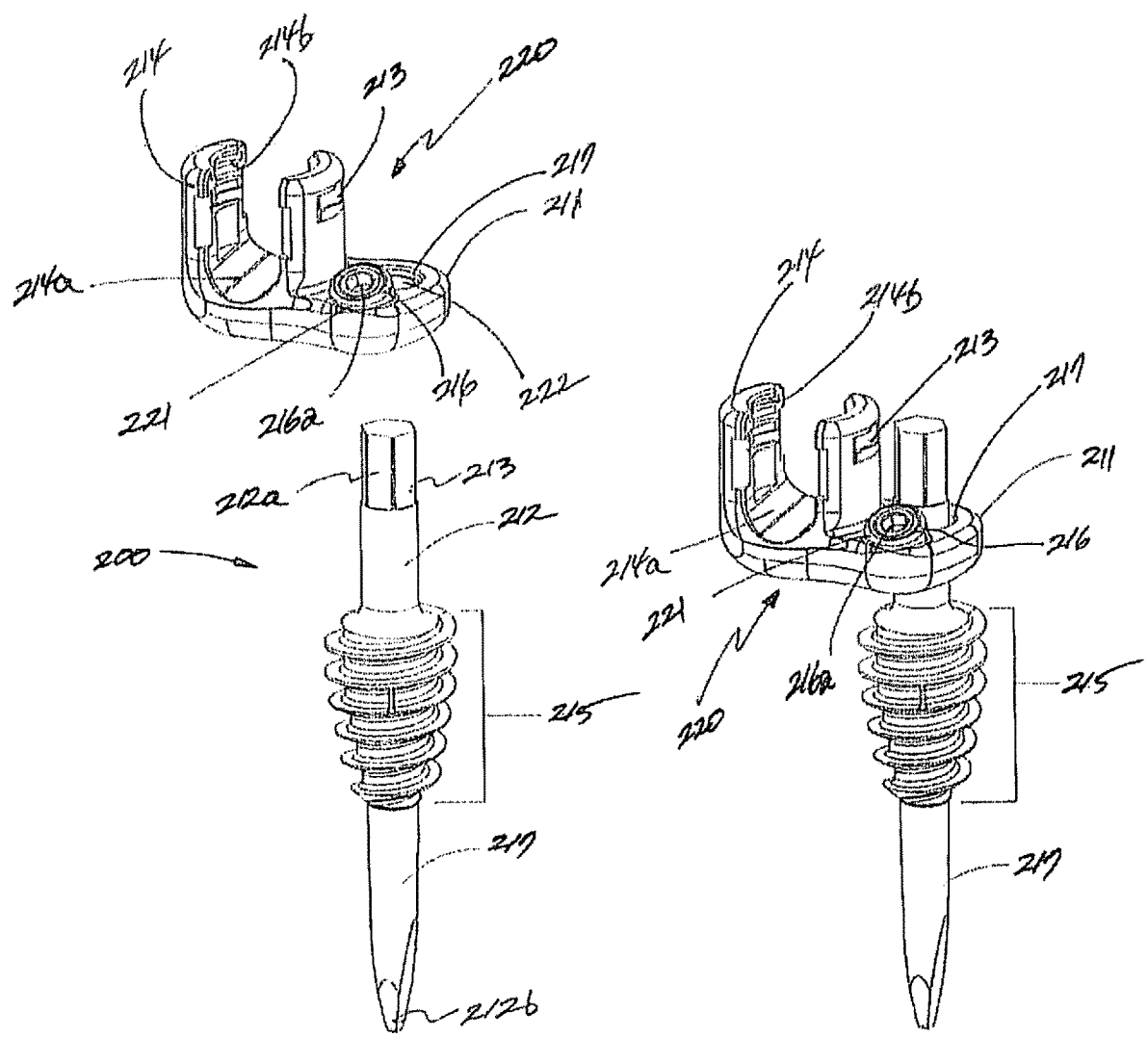
FIG. 16 is a perspective view of a modular screw in accordance with another embodiment of the present disclosure with a housing assembly and a post separated.
FIG. 17 is a perspective view of the modular screw of FIG. 16.

With reference now to FIGS. 16 and 17, there is illustrated a modular screw including a housing assembly 220 and a post 200 in accordance with another embodiment of the present disclosure. The housing assembly 220 is selectively securable with the post 200. The housing assembly 220 includes a base portion 211 including a head portion 214, a receiving portion 217, and a securing portion 221. The head portion 214 extends proximally from the base portion 211, and defines a slot 214a configured to receive, e.g., a spinal rod or a band (not shown). The slot 214a may include an arcuate profile to facilitate securement of the spinal rod therein. The head portion 214 includes inner walls 214b having threads configured to threadably receive a set screw (not shown) to secure the spinal rod in the slot 214a. The inner walls 214b may further define recesses or notches 213 configured to engage an instrument (e.g., a rod reducer).

With continued reference to FIGS. 16 and 17, the securing portion 221 defines a first bore (not shown) and includes a set screw 216 dimensioned to be threadably received in the first bore. The receiving portion 217 defines a second bore 222 and a split ring (not shown) defining a slit (not shown) configured to enable radial contraction and expansion of the split ring to selectively engage a head 212 of the post 200. The receiving portion 217 further defines an annular groove (not shown) concentrically arranged with the second bore 122. The split ring is mounted in the annular groove. The annular groove inhibits axial displacement of the split ring relative to the base portion 211. The split ring is transitionable between a radially expanded state and a radially contracted state. The second bore 222 and the split ring are dimensioned to receive the head 212 of the post 200 therethrough. Under such a configuration, when the set screw 216 is threadably received in the first bore, the set screw 216 engages the split ring and transitions the split ring to the contracted state, which, in turn, frictionally secures the base portion 211 on a position along a length of the head 212. When the set screw 216 is threadably received in the first bore, the set screw 216 engages at least a portion of the split ring disposed in the second bore 222, which, in turn, causes radial contraction of the split ring to frictionally engage the head 212 of the post 200. In this manner, the first assembly 212 may be selectively secured at a position along a length of the head 212 of the post 200. The set screw 216 includes a proximal portion 216a defining a cavity 216a having, e.g., a hex, key feature for non-slip engagement with a driver or other instrument (not shown) to drive the set screw 216. It is contemplated that the cavity 216a may have any suitable configuration such as, e.g., slotted, square, star, or a Phillips head, for engagement with the driver.

The post 200 includes a head 212 having a proximal portion 212a and a distal portion 212b. The proximal portion 212 includes a multi-faceted outer surface 213 configured to engage a tool (not shown). The proximal portion 212a is connected to the tapered portion 215. The tapered portion 215 and the shank 217 are substantially identical to the tapered portion 15 and the shank 17 of the post 500, and thus, will not be described herein. The method of use and operation of the post 200 is substantially identical to the method of use and operation of the post 500, and thus, will not be described herein.

Figure 18:
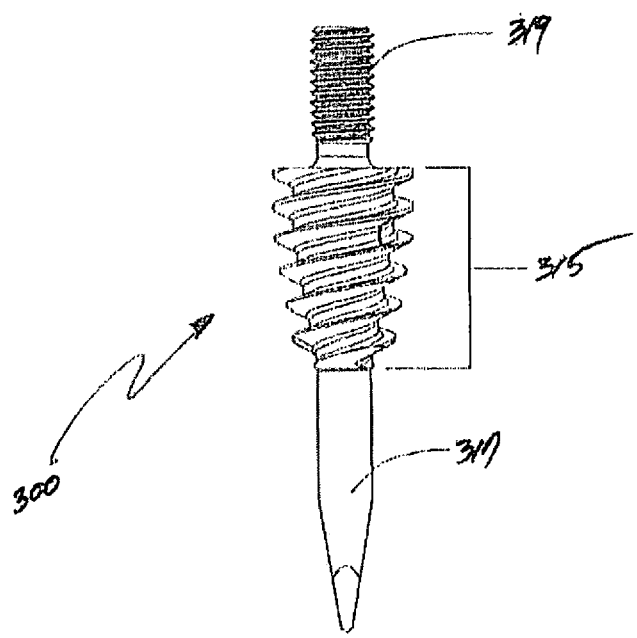
FIG. 18 is a side view of a post for use with a modular screw assembly in accordance with another embodiment of the present disclosure.
Figure 19:
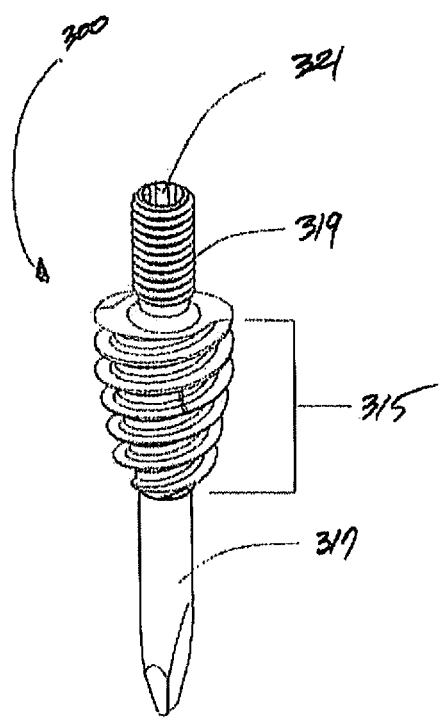
FIG. 19 is a perspective view of the post of FIG. 18.

With reference now to FIGS. 18 and 19, there is shown a post 300 in accordance with another embodiment of the present disclosure. The post 300 is substantially identical to the post 200 described hereinabove. Specifically, the post 300 includes a tapered portion 315 and a shank 317 extending distally from the tapered portion 315. However, the post 300 includes a threaded shank 319 proximal of the tapered portion 315. The threaded shank 319 includes external threads and defines a cavity 321 having, e.g., a hex, key feature for non-slip engagement with a driver or other instrument (not shown) to drive the post 300. It is contemplated that cavity 321 may have any suitable configuration such as, e.g., slotted, square, star, or a Phillips head, for engagement with the driver. The method of use and operation of the post 300 is substantially identical to the method of use and operation of the posts 200, 500, 600 described hereinabove, and thus, will not be described herein.

Figure 20:
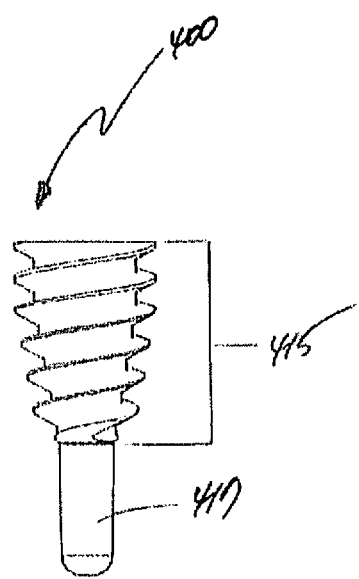
FIG. 20 is a side view of a post for use with a modular screw assembly in accordance with another embodiment of the present disclosure.
Figure 21:
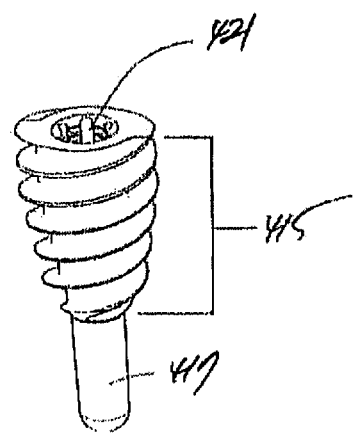
FIG. 21 is a perspective view of the post of FIG. 20.

With reference now to FIGS. 20 and 21, there is shown a post 400 in accordance with another embodiment of the present disclosure. The post 400 is substantially identical to the post 500 in that the post 400 includes a tapered portion 415 and a shank 417 extending distally from the tapered portion 415. However, the post 400 does not include a head as shown in posts 200, 300, 500, 600. Rather, the tapered portion 415 defines a cavity 421 having, e.g., a hex, key feature for non-slip engagement with a driver or other instrument (not shown) to drive the post 400. It is contemplated that cavity 421 may have any suitable configuration such as, e.g., slotted, square, star, or a Phillips head, for engagement with the driver.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A modular screw comprising:
   a first assembly including a base portion having a head portion defining a slot dimensioned to receive a spinal rod, a securing portion defining a first bore and including a first set screw threadably received in the first bore, and a receiving portion defining a second bore; and
   a second assembly operatively associated with the first assembly, the second assembly including:
      a first post defining a cavity;
      a second post including an engaging portion rotatably received in the cavity of the first post, the second post dimensioned to be received through the second bore of the receiving portion of the first assembly such that when the first set screw of the securing portion is received in the first bore of the securing portion, the first set screw secures the base portion of the first assembly to the second post; and
      an elongate screw threadably engageable with the second post, wherein the elongate screw received in the second post causes radial expansion of the engaging portion of the second post, which, in turn, causes the engaging portion to be affixed to the cavity of the first post.

2. The modular screw according to claim 1, wherein the engaging portion of the second post and the cavity of the first post have a ball and socket configuration.

3. The modular screw according to claim 1, wherein the engaging portion of the second post defines a slit configured to enable radial expansion of the engaging portion.

4. The modular screw according to claim 1, wherein the receiving portion of the first assembly defines an annular groove concentrically arranged with the second bore.

5. The modular screw according to claim 1, wherein the second post defines internal threads configured to threadably engage the elongate screw.

6. The modular screw according to claim 1, wherein the receiving portion of the first assembly includes a ring defining a slit configured to provide radial contraction and expansion of the ring, the ring configured to contract when the first set screw is threadably received in the first bore of the securing portion.

7. The modular screw according to claim 1, wherein a first longitudinal axis defined by the first bore of the first assembly defines an acute angle with respect to a second longitudinal axis defined by the second bore.

8. The modular screw according to claim 1, wherein the first post of the second assembly includes external threads along a length of the first post.

9. The modular screw according to claim 1, wherein at least a portion of the first post is tapered along a length thereof.

10. The modular screw according to claim 9, wherein the at least a portion of the first post extends at least a quarter of the length of the first post.

11. The modular screw according to claim 1, wherein the first post of the second assembly includes an inner surface having a keyed surface distal of the cavity.

12. The modular screw according to claim 1, wherein the head portion of the first assembly defines a lateral opening configured to receive a band therethrough.

13. The modular screw according to claim 1, wherein the head portion of the first assembly includes inner walls defining internal threads configured to threadably engage a set screw configured to secure the spinal rod received in the slot.

14. The modular screw according to claim 1, wherein the second post is configured for a polyaxial range of motion with respect to the first post, the polyaxial motion defines an angle with respect to a longitudinal axis defined by the first post in the range of about 15 degrees and about 60 degrees.

15. A modular screw comprising:
a first assembly including a base portion including a first set screw and a head portion configured to receive a spinal rod, the base portion defining a first bore configured to threadably receive the first set screw, and a second bore; and a second assembly including a first post configured to be at least partially received in tissue, a second post operatively associated with the first post, and an elongate screw operatively coupled with the second post to secure a relative orientation of the second post with respect to the first post, wherein the second post is dimensioned to be received in the second bore of the first assembly to selectively position the base portion of the first assembly along a length of the second post, and wherein tightening the first set screw secures the base portion of the first assembly to the second post at the selected position.

16. The modular screw according to claim 15, wherein the first bore of the base portion defines a first axis and the second bore of the base portion defines a second axis, wherein the first and second axes define an acute angle with respect to each other.

17. The modular screw according to claim 15, wherein the second post of the second assembly includes an engaging portion transitionable between a radially expanded state and a radially contracted state, wherein the engaging portion configured to maintain the orientation of the second post with respect to the first post when the engaging portion is in the radially expanded state.

18. The modular screw according to claim 15, wherein the first post includes a tapered portion extending along a length of the first post.

19. The modular screw according to claim 18, wherein the tapered portion extends partially along the length of the first post.

20. The modular screw according to claim 19, wherein the tapered portion includes external threads.

* * * * *